United States Patent
Shim (10) Patent No.: US 10,213,296 B2
(45) Date of Patent: Feb. 26, 2019

(54) GRAFT INCLUDING OSSEOUS TISSUE AND CARTILAGE TISSUE FOR AUGMENTATION RHINOPLASTY, AND METHOD OF PERFORMING AUGMENTATION RHINOPLASTY USING THE GRAFT

(71) Applicant: Min Bo Shim, Gyeonggi-do (KR)

(72) Inventor: Min Bo Shim, Gyeonggi-do (KR)

( * ) Notice: Subject to any disclaimer, the term of this patent is extended or adjusted under 35 U.S.C. 154(b) by 0 days.

(21) Appl. No.: 15/076,938

(22) Filed: Mar. 22, 2016

(65) Prior Publication Data

US 2017/0112615 A1   Apr. 27, 2017

(30) Foreign Application Priority Data

Oct. 23, 2015   (KR) .................. 10-2015-0148015

(51) Int. Cl.
*A61F 2/18*   (2006.01)
*A61F 2/00*   (2006.01)

(52) U.S. Cl.
CPC ............ *A61F 2/186* (2013.01); *A61F 2/0059* (2013.01); *A61F 2310/00359* (2013.01)

(58) Field of Classification Search
CPC ................... A61F 2/186; A61F 2/0059; A61F 2310/00359
See application file for complete search history.

(56) References Cited

FOREIGN PATENT DOCUMENTS

| KR | 10-2005-0042749 | 5/2005 |
| KR | 10-2013-0120112 | 11/2013 |
| KR | 10-2014-0104252 | 8/2014 |
| KR | 10-2015-0010240 | 1/2015 |

OTHER PUBLICATIONS

Sabeti et al. "A New Technique for Reconstruction of the Nasal Dorsum: Underlay Autografting." Archives of Facial Plastic Surgery, vol. 4, No. 3, Jan. 2002, pp. 141-148.*
Grigoryants et al. "The Use of Short Spreader Grafts in Rhinoplasty for Patients with Thick Nasal Skin." Aesthetic Plastic Surgery, vol. 37, No. 3, 2013, pp. 516-520.*
Huang et al. "Endoscopic Placement of Spreader Grafts in the Nasal Valve." Otolaryngology-Head and Neck Surgery, vol. 134, No. 6, 2006, pp. 1001-1005.*
Zaidi et al. "Investigating the Case of Human Nose Shape and Climate Adaptation." PLOS Genetics, vol. 13, No. 3, 2017.*

(Continued)

*Primary Examiner* — David Isabella
*Assistant Examiner* — Rokhaya Diop
(74) *Attorney, Agent, or Firm* — King & Spalding LLP (57) ABSTRACT

A graft for augmentation rhinoplasty, the graft including bone tissue and cartilage tissue, and a method of performing augmentation rhinoplasty by using the graft are disclosed. According to the disclosure, autologous tissue for augmentation rhinoplasty can be obtained in a sufficient amount to so that a nose can be uplifted to a desired height. In addition, rhinoplasy can be easily performed, resulting in a naturally-shaped nose. As the osseous tissue is grafted on the originally existing osseous tissue and cartilage tissue is grafted on the originally existing cartilage, the construction of the original anatomical structure of the nose can be allowed and there is an effect that there is no side effect such as a foreign body reaction.

17 Claims, 9 Drawing Sheets

(56) References Cited

OTHER PUBLICATIONS

Fry, Hunter. "Nasal Skeletal Trauma and the Interlocked Stresses of the Nasal Septal Cartilage." British Journal of Plastic Surgery, vol. 20, 1967, pp. 146-158.*
Baek et al. "Rhinoplasty Using Rib Chondro-Osseous Graft in Asian Patients." Journal of Craniofacial Surgery, vol. 21, No. 4, 2010, pp. 1122-1125.*
Kim, et al. "Cultured Chondrocyte and Porcine Cartilage-Derived Substance (PCS) Construct as a Possible Dorsal Augmentation Material in Rhinoplasty: A Preliminary Animal Study." Journal of Plastic, Reconstructive & Aesthetic Surgery, vol. 68, No. 5, 2015.*
Baek et al., "Rhinoplasty Using Rib Chondro-Osseous Graft in Asian Patients," the Journal of Craniofacial Surgery, 21(4), pp. 1122-1125, Jul. 2010.
Cingi et al., "Augmentation mentoplasty with osteocartilaginous nasal graft," Otolaryngology—Head and Neck Surgery, 143, pp. 549-553, 2010.
Orak et al., "Use of Osseocartilaginous Paste Graft for Refinement of the Nasal Dorsum in Rhinoplasty," Aesth Plast Surg, 37, pp. 876-881, 2013.

* cited by examiner

GRAFT INCLUDING OSSEOUS TISSUE AND CARTILAGE TISSUE FOR AUGMENTATION RHINOPLASTY, AND METHOD OF PERFORMING AUGMENTATION RHINOPLASTY USING THE GRAFT

CROSS-REFERENCE TO RELATED APPLICATION

This application claims the benefit of Korean Patent Application No. 10-2015-0148015, filed on Oct. 23, 2015, in the Korean Intellectual Property Office, the disclosure of which is incorporated herein in its entirety by reference.

BACKGROUND

1. Field

One or more exemplary embodiments relate to a graft for augmentation rhinoplasty, the graft including osseous tissue and cartilage tissue, and a method of performing augmentation rhinoplasty using the graft.

2. Description of the Related Art

Types of rhinoplasty are very diverse, and various surgery procedures for rhinoplasty can be carried out depending on a patient's condition, request, a type of modification, a type of previous rhinoplasty, or a surgical method of previous rhinoplasty. Rhinoplasty is not only a surgery procedure for uplifting a nose or correcting a twisted nose, but also a surgery procedure performed in a wide range of fields including a correction of congenital deformity, a treatment for a defect caused by an accident, a reconstruction of the nose after removal of cancer tissue, and the like. For example, rhinoplasty may be carried out for orthodontic treatment purposes or cosmetic purposes when a nose is congenitally flat, a shape of the nose is changed, or a defect or a change occurs in a nose area due to a tumor surgery or the like.

Rhinoplasty is typically carried out by inserting materials to the nose, and types of the materials used herein can be divided into a graft and an implant. The graft may consist of a bone and a cartilage, and types of the bone can be divided into a cartilage bone, which is formed through ossification of the cartilage, and a membranous bone, which is formed through direct ossification of mesenchymal tissue. In general, the membranous bone, such as a cranial bone, is widely used for autogenous bone grafting in view of advantages of high survival rates and low absorption rates. In addition to the membranous bone, the cartilage bone, such as an iliac bone or a costal bone, may be also used for autogenous bone grafting. The cartilage has advantages of low absorption rates, survivability without a blood supply, and ease of shaping, compared to osseous tissue, and in this regards, nasal septum cartilage, auricular cartilage, or costal cartilage may be used mainly for augmentation rhinoplasty. In the case of using a bone graft among the grafts, the bone graft is not easily displaced based on firm bond fixation thereof, and furthermore, the bone graft can be obtained in a large amount without causing a foreign body reaction. However, bone fractures may occur with the bone graft, and there are difficulties in collecting the bone graft, leaving a bond graft donor site wound, handling the bone graft, dealing with large absorption, and lacking flexibility. In the case of using septal cartilage among autologous chondrocyte, the septal cartilage is easy to use, but has disadvantages of small availability and a difficulty in forming a firm line of nasal dorsum. The implant means an artificial inert material that can be left in body tissue for a long time without causing any chemical changes in the body tissue, and examples thereof include a silicone implant, a gore-tex implant, a mersiliene implant, a mesh-type implant, AlloDerm, and Proplast implant. However, since the implant is an artificial implant, the implant may cause a foreign body reaction and side effects, such as discolored skin, and displacement, olisthy, or inflammation after performing the method of augmentation rhinoplasty.

Therefore, there is still a need to develop a graft using autologous tissue to prevent a side reaction, such as a foreign body reaction, and obtain firm autologous tissue in a sufficient amount, and a method of performing augmentation rhinoplasty by using the graft.

SUMMARY OF THE INVENTION

One or more exemplary embodiments include a graft for augmentation rhinoplasty, the graft including: a first compartment consisting of osseous tissue; and a second compartment consisting of cartilage tissue and undergoing cartilaginification through an osteocartilaginous junction to the first compartment.

One or more exemplary embodiments include a method of performing augmentation rhinoplasty by using the graft. In an exemplary embodiment, the method includes: providing at least one first graft by isolating at least one part of a nasal septum from the nose of a subject, wherein the at least one first graft comprises both a first compartment consisting of osseous tissue and a second compartment consisting of cartilage tissue; manufacturing a second graft for forming a line of nasal dorsum of the subject by excising a part of the at least one first graft, wherein the second graft comprises both a first compartment consisting of osseous tissue and a second compartment consisting of cartilage tissue; preparing at least two pieces of the first graft by cutting another part of the at least one first graft, which remains after the manufacturing of the second graft, into at least two pieces; forming two lines of nasal dorsum by inserting the second graft into a nasal dorsum of the subject; and raising the nasal dorsum in a dorsal direction by inserting the at least two pieces of the first graft into a space positioned in a ventral direction with respect to the second graft that is inserted into the nasal dorsum of the subject.

BRIEF DESCRIPTION OF THE DRAWINGS

These and/or other aspects will become apparent and more readily appreciated from the following description of the embodiments, taken in conjunction with the accompanying drawings in which:

As shown in FIG. 9A, the line of nasal dorsum refers to two imaginary lines from inner edges of both eyebrows to a tip defining point of the nose when viewing the front of the face. FIG. 9B presents a diagram illustrating a side view of the human nasal septum.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present inventive concept, there is provided a graft for augmentation rhinoplasty, the graft including: a first compartment consisting of isolated osseous tissue; and a second compartment consisting of isolated cartilage tissue and connected with the first compartment through an osteocartilaginous junction.

The term "graft" as used herein can be interchangeably used with a transplant, and refers to an organ or tissue of a subject for transplantation. For example, the graft may include an autotransplant and an allograft, wherein the autotransplant is prepared by transplanting autologous tissue present in a specific site (i.e., a donor site) of a subject into another site of the same subject, and the allograft is prepared by being transplanted from a different subject belonging to the same homogeneity. The graft may be isolated from the subject, or may be prepared as artificial bone or artificial cartilage according to methods widely known in the art. For example, cells of the osseous tissue or the cartilage tissue may be obtained from a patient, and cultured in vitro or in vivo. Following the culturing of the cells, the graft may be, for example, prepared according to a 3D printing technique or a technique for inducing formation of the osseous tissue or the cartilage tissue. Alternatively, the graft may be prepared by using biocompatible polymer materials. Thus, in an exemplary embodiment, the graft may be prepared by culturing the isolated bone cells (i.e., osteocytes)) and the isolated cartilage cells (i.e., chondrocytes) in vitro or in vivo. That is, after the isolated osteocytes and the chondrocytes are inoculated into a culture container to culture the same in a 3-dimensional manner, thereby preparing the graft. In addition, the culture may be cultured by using a biocompatible polymer scaffold as a substrate. The biocompatible polymer may include a synthetic polymer or a natural polymer. Examples of the synthetic polymer include poly (lactic acid) (PLA), poly(glycolic acid) (PGA), poly(ε-caprolactone) (PCL), or poly(lactic-co-glycolic acid) (PLGA). Examples of the natural polymer include collagen, albumin, poly(amino acid), cellulose, agarose, alginate, heparin, hyaluronic acid, or chitosan. A method of manufacturing the graft is described in the following documents: "Scaffolds in tissue engineering bone and cartilage (written by D. W. Hutmacher)" Biomaterials, 21, 2529-2543 (published in 2000), "Cartilage tissue engineering with silk scaffolds and human articular chondrocytes (written by Y. Z. Wang, D. J. Blasioli, H. J. Kim, H. S. Kim, and D. L. Kaplan)" Biomaterials, 27, 4434-4442 (published in 2006), or "Tissue engineering and cartilage regeneration for auricular reconstruction (written by A. Ciorba and A. Martini)" International Journal of Pediatric Otorhinolaryngology, 70, 1507-1515 (published in 2006). All the documents are referred to as reference in the present specification. The coaptation of the graft may be followed by the manufacture of each of the osseous tissue and the cartilage tissue, or the graft, to which osseous tissue and the cartilage tissue are coaptated, may be manufactured.

In an exemplary embodiment, the graft may be isolated from a nasal septum. In another exemplary embodiment, the graft may be a nasal osteocartilaginous graft.

The term "nasal septum" as used herein refers to a partition wall in a human's nose that separates the left and right nasal cavity, and is a structure containing bone and cartilage to support nasal dorsum and a nasal tip and covered with a mucous membrane.

Figure 9A:
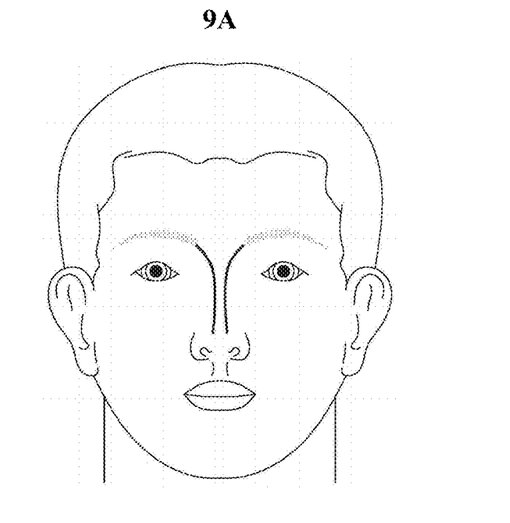
FIGS. 9A and 9B are images depicting the human line of nasal dorsum (FIG. 9A) and the human nasal septum (FIG. 9B).

The term "line of nasal dorsum" as used herein refers to two imaginary lines having a width of a certain degree therebetween, and in detail, the line of nasal dorsum refers to two imaginary lines from inner edges of both eyebrows to a tip defining point of the nose when viewing the front of the face, as shown in FIG. 9A. The width of the line of nasal dorsum generally refers to a width between two imaginary lines in the center of the line of nasal dorsum.

Figure 9B:
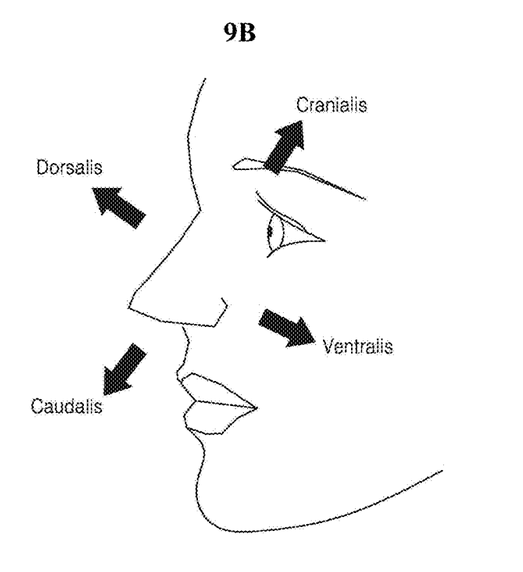

In the present specification, descriptions of the direction of the anatomical location are provided by referring to FIG. 9B, which is a diagram illustrating a side view of the human nasal septum.

In an exemplary embodiment, the graft (e.g., 101 of FIG. 1 or 2) may have a longitudinal length in a range of about 1 cm to about 9 cm, about 4 cm to about 8 cm, or about 5 cm to about 7 cm. In addition, the graft (e.g., 101 of FIG. 1 or 2) may have a vertical length in a range of about 2 mm to about 15 mm, about 2 mm to about 10 mm, about 3 mm to about 9 mm, or about 3 mm to about 5 mm. In addition, the graft (e.g., 101 of FIG. 1 or 2) may have a height in a range of about 0.5 mm to about 3 mm, about 0.5 mm to about 1.5 mm, or about 0.5 mm to about 1.0 mm. When the graft (e.g., 101 of FIG. 1 or 2) is put on a nasal dorsum of a subject, the longitudinal direction of the graft means a direction parallel to the line of nasal dorsum, the vertical direction of the graft means a direction perpendicular to the line of nasal dorsum, and the height of the graft means a value defining a volume of the graft. The graft may have a square shape that is defined by the longitudinal direction and the vertical direction, and may have a circular shape at the tip of the longitudinal direction.

The osseous tissue included in the graft may include, for example, a part of nasal bone, and the cartilage tissue included in the graft may include, for example, a part of nasal septum cartilage, a part of upper lateral nasal cartilage, and/or a part of nasal bone.

At least one part of isolated mucoperiosteum and/or mucoperichondrium may be or may not be attached to a surface of the first compartment and/or the second compartment of the graft. For example, the mucoperiosteum and/or the mucoperichondrium may be or may not be removed from the graft. In an exemplary embodiment, periosteum and/or perichondrium may not be removed from the graft, and in this regard, a donor site still exists and the occurrence of perforations in the nasal septum may be prevented. However, in another exemplary embodiment, periosteum and/or perichondrium may be already damaged (e.g., torn) before surgery, and in this case, the graft may be isolated along with the periosteum and/or perichondrium. Accordingly, the graft according to an exemplary embodiment may include the periosteum and/or perichondrium that are partially attached to the surface of the graft. In general, it is known that bone and cartilage absorb nutrients through the mucoperiosteum and/or the mucoperichondrium. However, it is observed that there is no effect on the survival of the graft according to an exemplary embodiment in the absence of the mucoperiosteum and/or the mucoperichondrium, and in addition, absorption or deformation of the graft is not observed through 1-year observation and confirmation.

In addition, about ½ to about ⅕ or about ½ to about ¼ of the graft is occupied by the first compartment consisting of the osseous tissue. For example, about 20% to about 50% of the total longitudinal length of the graft is occupied by the first compartment while the rest of the total longitudinal length of the graft is occupied by the second compartment. The cartilage tissue included in the graft may include hyaline cartilage, and the osseous tissue included in the graft may include membranous bone tissue.

In an exemplary embodiment, the graft may be provided as a kit, wherein the kit additionally includes a plurality of bond pieces and/or cartilage pieces. Thus, the graft according to an exemplary embodiment may be used to provide a kit for augmentation rhinoplasty, the kit including a plurality of bone pieces and/or cartilage pieces. Such bone pieces or cartilage pieces may be a part of the same tissue as the osseous tissue or cartilage tissue of the graft, or may be prepared by cutting tissue, which is isolated from different tissue from the osseous tissue or cartilage tissue of a subject, into an appropriate size. In addition, such bone pieces and/or cartilage pieces may be prepared in the same manner as in the manufacture of the graft, and that is, cells of the osseous tissue or the cartilage tissue are obtained from a patient, and then, cultured in vitro or in vivo, thereby inducing generation of the osseous tissue or the cartilage tissue. Such bone pieces and/or cartilage pieces may include, for example, at least 2, at least 4, at least 8, at least 10, or at least 15 pieces, and may be prepared in a smaller size than that of the graft according to an exemplary embodiment. In addition, such bone pieces and/or cartilage pieces may have an amorphous shape or a spherical shape. Use of the bone pieces and/or cartilage pieces will be described in the following exemplary embodiments.

According to another aspect of the present inventive concept, there is provided method of performing augmentation rhinoplasty by using the graft. In an exemplary embodiment, the method includes: providing at least one first graft by isolating at least one part of a nasal septum from the nose of a subject, wherein the at least one first graft includes both a first compartment consisting of osseous tissue and a second compartment consisting of cartilage tissue; manufacturing a second graft for forming a line of nasal dorsum of the subject by excising a part of the at least one first graft, wherein the second graft includes both a first compartment consisting of osseous tissue and a second compartment consisting of cartilage tissue; preparing at least two pieces of the first graft by cutting another part of the at least one first graft, which remains after the manufacturing of the second graft, into at least two pieces; forming two lines of nasal dorsum by inserting the second graft into a nasal dorsum of the subject; and raising the nasal dorsum in a dorsal direction by inserting the at least two pieces of the first graft into a space positioned in a ventral direction with respect to the second graft that is inserted into the nasal dorsum of the subject.

The graft used for performing augmentation rhinoplasty is defined the same as described above. In an exemplary embodiment, the second graft used in the method corresponds to the graft for augmentation rhinoplasty as described above in connection with the graft according to an exemplary embodiment, and the pieces of the first graft used in the method correspond to the bone pieces or the cartilage pieces as described above in connection with the graft according to an exemplary embodiment. Thus, although it is described that the second graft and the pieces of the first graft used in the method in an exemplary embodiment are isolated from the human body, the second graft and the pieces of the first graft may be prepared by using a biocompatible polymer scaffold as a substrate for culturing the isolated osteocytes and the isolated chondrocytes in vitro or in vivo, as in the case of the graft for augmentation rhinoplasty. That is, the second graft and the pieces of the first graft may be prepared by using a biocompatible polymer scaffold as a substrate for culturing the isolated osteocytes and the isolated chondrocytes in vitro or in vivo, rather than being isolated from the human body. In this case, the isolating and manufacturing of the graft may be omitted in the method according to an exemplary embodiment. In addition, the second graft and the pieces of the first graft may be provided as a kit including the same.

In an exemplary embodiment, the second graft may have a longitudinal length in a range of about 3 cm to about 9 cm, a vertical length in a range of about 2 mm to about 15 mm, and a height in a range of about 0.5 mm to about 3 mm. The osseous tissue included in the second graft may include a part of the nasal bone, and the cartilage tissue included in the second graft may include a part of the nasal septum cartilage and a part of the upper lateral nasal cartilage. About ½ to about ⅕ of the longitudinal length of the second graft is occupied by the first compartment consisting of the osseous tissue. The cartilage tissue included in the second graft may include hyaline cartilage tissue. The first and second compartments of the second graft may be connected to each other through an osteocartilaginous junction.

The method according to an exemplary embodiment may further include performing a preoperative treatment on a patient. The performing of the preoperative treatment may include: evaluating a preoperative patient and performing preoperative care on a patient. In an exemplary embodiment, the evaluating of the preoperative patient may include evaluating an ideal condition of the nose. For example, the evaluating of the preoperative patient may include identifying a current nose shape of the patient and determining a desired nose shape that can be made through surgery to determine plans for surgery or treatment. In terms of nasal index, the ideal condition of the nose may be generally determined by calculating a size of the nose, a width of the nasal dorsum, a nasofrontal angle, or a nasolabial angle. For example, although not limited thereto, the size of the nose is considered ideal in the following cases: a case where the nose occupies about ⅓ of the whole face in view of a horizontally-partitioned face or about ⅕ of the whole face in view of a vertically-partitioned face; a case where a width of the nasal dorsum is in a range of about 9 mm to about 13 mm; a case where an angle between columella and ala of the nose is about 2.1°; a case where a starting point for uplifting the nose is at wrinkles on the upper eyelid of the subject; a case where a height of the nasal dorsum and the nasal tip is less than 2 mm; a case where a nasofrontal angle is in a range of about 135° to about 140°; and a case where a nasolabial angle is in a range of about 90° to about 95°. The cases described above are considered merely as a reference in terms of determining plans for surgery or treatment. Thus, the plans for surgery or treatment may be appropriately determined by one of ordinary skill in the art according to a patient's condition or medical history, and the plans determined therein are not limited to the cases described above. Following the determining of the plans for surgery or treatment, the performing of the preoperative treatment on the patient may be carried out. The performing of the preoperative treatment on the patient may include: sterilizing a patient and anesthetizing the patient. The sterilizing of the patient may be performed on the patient lying on an operating table. Here, the head of the patient is positioned to be slightly raised from the operating table. In this posture, the patient's entire face and inner nose are cleaned, and the face, except a surgical site, is covered with a surgical drape. The anesthetizing of the patient may be performed by general anesthesia and/or local anesthesia. General anesthesia may include steps of premedication, induction of anesthesia, and/or maintenance of anesthesia, and may be carried out through intravenous injection or inhalation anesthesia. Examples of a general anesthetic drug include zoletil, xylazine, zolazepam, halothane, desflurane, isoflurane, thiopental, propofol, and midazolam. Local anesthesia may be performed generally by using a local anesthetic drug and a vasoconstrictor in combination. Examples of the local anesthetic drug include lidocaine, procaine, chloroprocaine, tetracaine, dibucaine, etidocaine, bupivacaine, and mepivacaine. Examples of the vasoconstrictor include epinephrine, norepinephrine, levonordefrin, and phenylephrine. In addition, an analgesic may be additionally used, and examples thereof include nalbuphine hydrochloride and diclofenac sodium. The type, dosage, administration, route, or injection time of the anesthetic drugs above may be easily determined by one of ordinary skill in the art according to the patient's condition. For example, when using lidocaine and epinephrine in combination, lidocaine is used at a concentration in a range of about 0.5% to about 2% and a concentration ratio of epinephrine to lidocaine is in a range of about 1:50,000 to about 1:2,000,000. When using lidocaine alone, about 3 mg (per patient's kilogram) of lidocaine is allowed, and in the case of adults, about 200 mg (20 cc of 1% lidocaine, per patient's kilogram) of lidocaine is allowed. When using lidocaine in combination with epinephrine, about 7 mg (per patient's kilogram) of lidocaine is allowed, and in the case of adults, about 500 mg (25 cc of 2% lidocaine, per patient's kilogram) of lidocaine is allowed. Local anesthesia may be performed on a site between alar cartilage and upper lateral nasal cartilage.

Next, the isolation and manufacture of the graft may be performed. The isolation of the graft may be performed by providing at least one first graft by isolating at least one part of the nasal septum from the nose of the subject, wherein the at least one first graft comprises both the first compartment consisting of osseous tissue and the second compartment consisting of cartilage tissue. One of ordinary skill in the art may use an osteotome to perform the isolation of the graft. A method of approaching the graft will be described below.

In an exemplary embodiment, the isolating of the at least one part of the nasal septum may be carried out by isolating one complex including a part of nasal septum cartilage, a part of upper lateral nasal cartilage, and a part of nasal bone. The first graft may be isolated by isolating one complex including the entire nasal septum cartilage, the entire upper lateral nasal cartilage, and the entire nasal bone. The isolating of the at least one part of the nasal septum may be carried out multiple times so that the entire nasal septum cartilage, the entire upper lateral nasal cartilage, and the entire nasal bone may be isolated from the nose of a subject. In this case, at least two first grafts may be isolated from the nose of a subject. When at least two first grafts are isolated, at least one of them is configured to include both the first compartment consisting of the osseous tissue and the second compartment consisting of the cartilage tissue.

In another exemplary embodiment, the isolating of the at least one part of the nasal septum may be performed in a way that a nasal septum (e.g., nasal septum cartilage) remains at least about 0.5 cm in a caudal direction, and remains in a range of about 0.5 cm to about 2.5 cm, about 1.0 cm to about 2.0 cm, or about 1.2 cm to about 1.8 cm in a dorsal direction. The presence of nasal septum cartilage on a donor site with about 0.5 cm or less in the caudal direction may be advantageous for a sufficient graft harvesting. As of the method used in the related art, if nasal septum cartilage having a length of about 1 cm remains on the nasal septum, a length of a cartilage site on the graft may be shorter than a total length of a dorsal cartilage site of the donor site, and thus augmentation rhinoplasty may not be done in an efficient manner. In addition, the presence of nasal septum cartilage on a donor site with about at least 1.5 cm or more in the dorsal direction of the nasal septum may be advantageous to stabilize the shape of the nose after surgery. In this regard, even if the remaining nasal septum cartilage is smaller than the remaining nasal septum cartilage used in the existing surgery method in view of the caudal direction, problems associated with bearing capacity of nasal bridge of the nasal septum or bearing capacity of the graft do not occur. The remaining nasal septum at the donor site may then include a part of the nasal septum cartilage, a part of the upper lateral nasal cartilage, or a part of the nasal alar cartilage. The remaining nasal septum at the donor site may then be served as a space for supporting the nose after surgery or fir supporting the graft inserted thereinto.

During the isolating of the at least one part of the nasal septum, at least one part of isolated mucoperiosteum and mucoperichondrium may be remained on the donor site of the subject. In an exemplary embodiment, due to the remained mucoperiosteum and mucoperichondrium, the occurrence of perforations in the nasal septum may be prevented. However, in another exemplary embodiment, periosteum or perichondrium may be already damaged (e.g., torn) before surgery, and in this case, the graft may be isolated along with the periosteum or the perichondrium. Accordingly, the graft according to an exemplary embodiment may include the periosteum or the perichondrium that are partially attached to the surface of the graft. In addition, when the periosteum or the perichondrium remains only one part of the nasal septum, the occurrence of perforations therein may be prevented, and in this case, one part of the nasal septum may be sacrificed to restore the periosteum or the perichondrium included in the other part of the nasal septum. In general, it is known that bone and cartilage absorb nutrients through the mucoperiosteum or the mucoperichondrium. However, it is observed that there is no effect on the survival of the graft according to an exemplary embodiment in the absence of the mucoperiosteum or the mucoperichondrium, and addition, absorption or deformation of the graft is not observed through 1-year observation and confirmation.

In an exemplary embodiment, following the inserting of the second graft into the nasal septum, the inserted second graft is manufactured to form a line of nasal dorsum having a width in a range of about 5 mm to about 15 mm or about 7 mm to about 12 mm or a width of 10 mm, between two lines of nasal dorsum in view of external appearance. The formation of the line of nasal dorsum means formation of a line of nasal dorsum newly made by augmentation rhinoplasty. That is, in addition to the line of nasal dorsum originally present on the nose of the subject, a new line of nasal dorsum is formed upon the insertion of the second graft. The second graft may be prepared by using a surgical instrument, such as an osteotome, on the first graft in consideration of the desired shape or size of the graft as described above. For example, one of ordinary skill in the art may appropriate adjust the size of the second graft in consideration of a patient's skin thickness or the like, so as to form the line of nasal dorsum having the width within the ranges above.

Next, pieces of the first graft may be manufactured by using the second graft that is remained after the manufacturing of the second graft. Such pieces of the first graft may include pieces of bone, cartilage, or cartilage tissue. The number and size of the pieces of the first graft may be appropriately determined by one of ordinary skill in the art to achieve the desired effects therefrom. The graft according to an exemplary embodiment may be a nasal osteocartilaginous graft including both the osseous tissue and the cartilage tissue, and can be used to sufficiently obtain a desired tissue. Thus, one of ordinary skill in the art may obtain materials for augmentation rhinoplasty in sufficient number and sizes by using the graft.

Following the manufacturing of the graft, the inserting of the second graft and the pieces of the first graft may be performed. The inserting of the second graft may be performed on a space below the nasal skin. Here, the above-described separation of the nasal septum and the insertion of the graft into the nasal septum may be performed by using appropriate surgical instruments or according to the approach method. The approach method may include an endonasal approach method or an external nasal approach method. In addition, the endonasal approach may include a delivery approach or a nondelivery approach. The nondelivery approach means a method of manipulating the alar cartilage without exposing the alar cartilage (i.e., the alar cartilage positioned at its own place) after making an intracartilaginous incision in the middle of a lateral crus of the alar cartilage. In the nondelivery approach, a line for the intracartilaginous incision is made to a relatively deep point to incise both a nasal mucous membrane and the alar cartilage, and then, cartilage posterior to the incision line is removed. Then, the alar cartilage is connected to a part or a total of a transfixion incision to manipulate cartilage posterior to a medial crus of the alar cartilage. The delivery approach means a method of manipulating a lateral crus of the alar cartilage by making two incision lines each on upper and lower parts of the surf alar cartilage. In the delivery approach, the alar cartilage may be subjected to marinal incision and intercartilagenous incision, followed by removal of the alar cartilage. The delivery approach may include, as in the case of the nondelivery approach, a step of performing transfixion incision, thereby ensuring a slightly better visual field. Meanwhile, the external nasal approach may be performed by connecting marinal and transcolumellar incisions. The transcolumellar incision may include Goodman's incision or stair step incision. In the external nasal approach, after the incision line is made, an incision (about 1 mm or 2 mm) is made on each of side walls of the nasal columella within the nose, thereby connecting two incision lines. The approach methods described herein are associated with augmentation rhinoplasty, and one of ordinary skill in the art may perform an appropriate approach method to separate or insert the graft according to a patient's condition and competence of the skilled person.

In the inserting of the second graft, the first compartment of the second graft may be arranged in a cranial direction, and the second compartment may be arranged in a caudal direction. In this regard, the osseous tissue included in the first compartment may be grafted on a site where the osseous tissue was originally present, and the cartilage tissue included in the first compartment may be grafted on a site where the cartilage was originally present, thereby constructing the original anatomical structure of the nose. In addition, the second graft may be inserted from a nasion until a site where the upper lateral nasal cartilage was present is reached.

Next, the inserting of the pieces of the first graft into the inserted second graft may be performed in a ventral direction to raise a height of the nasal dorsum in a dorsal direction. For example, in regard to the inserting of the pieces of the first graft, the small-sized pieces of the first graft or the small number of the pieces of the first graft may be inserted into second graft near the nasion. Alternatively, the large-sized pieces of the first graft or the great number of the pieces of the first graft may be inserted into second graft near the nasal tip. Here, the number of the pieces of the first graft to be inserted into the second graft may be, for example, at least two, at least 4, at least 8, at least 10, or at least 15.

The second graft or at least two pieces of the first graft may be performed by one of ordinary skill in the art to raise a height of the nose up to a desired level. For example, the second graft and at least two pieces of the first graft may be inserted to uplift a height of the nose by at least about 4 mm or at least about 7 mm, or in a range of about 4 mm to about 5 mm, about 4 mm to about 12 mm, or about 4 mm to about 10 mm, wherein the height is measured from the imaginary line connecting the nasal bone and the upper lateral nasal cartilage to the nasal skin. In augmentation rhinoplasty using the graft (e.g., a silicone material) of the related art, it is known that the insertion of the silicone material to uplift a height of the nose by at least 7 mm is in the risk of side effects. However, in augmentation rhinoplasty according to an exemplary embodiment, unlike the techniques of the related art, rhinoplasty to uplift a height of the nose by at least 7 mm is allowed without causing side effects. In addition, the inserting of the second graft and the inserting of the at least two pieces of the first graft may be performed in a way that a ratio of a length of the imaginary line connecting the nasion and the nasal tip to a height of the nasal tip is in a range of about 1:0.5 to about 1:0.8.

In an exemplary embodiment, nasal tip-plasty to support the nasal tip may be additionally performed. In the nasal tip-plasty, tissue (e.g., cartilage tissue) remained after the providing of the first graft for augmentation rhinoplasty, may be used. In addition, cartilage tissue manufactured by using the above-described isolated chondrocytes may be used for nasal tip-plasty, and in this case, the cartilage tissue for supporting the nasal tip may be provided in the form of a kit. In addition to the cartilage tissue, cartilage of other parts of the body, e.g., auricular cartilage or costal cartilage, may be used for nasal tip-plasty. In an exemplary embodiment, the cartilage tissue that remained after the providing of the first graft for augmentation rhinoplasty may be used for nasal tip-plasty. In the method of performing augmentation rhinoplasty according to an exemplary embodiment, the composite of the osseous tissue and the cartilage tissue is isolated at once, and thus the graft for augmentation rhinoplasty may be prepared in a sufficient amount. Furthermore, unlike the techniques of the related art, the cartilage graft for nasal-tip plasty may be obtained at once. That is, when performing nasal tip-plasty using the nasal septum cartilage in the related art, the graft consisting of nasal septum cartilage was not obtained enough for augmentation rhinoplasty, and thus cartilage of other parts of the body or implants (e.g., silicone materials) were used for augmentation rhinoplasty. Alternatively, when performing augmentation rhinoplasy using the nasal septum cartilage in the related art, the graft consisting of nasal septum cartilage was not obtained enough for natal tip-plasty, and thus cartilage of other parts of the body or implants (e.g., silicone materials) were used for natal tip-plasty. However, unlike the cases above, in the method according to an exemplary embodiment, the graft obtained from the nose of the subject can be used for both augmentation rhinoplasty and nasal tip-plasty.

After the completion of the inserting of the graft, a step of manually adjusting a position of the inserted graft and a step of suturing the incision lines may be performed. These steps and a step of performing a postoperative step may be appropriately performed by one of ordinary skill in the art.

Hereinafter, the present inventive concept will be described in further detail with reference to the following examples. However, these examples are for illustrative purposes only and are not intended to limit the scope of the present inventive concept.

Figure 1:
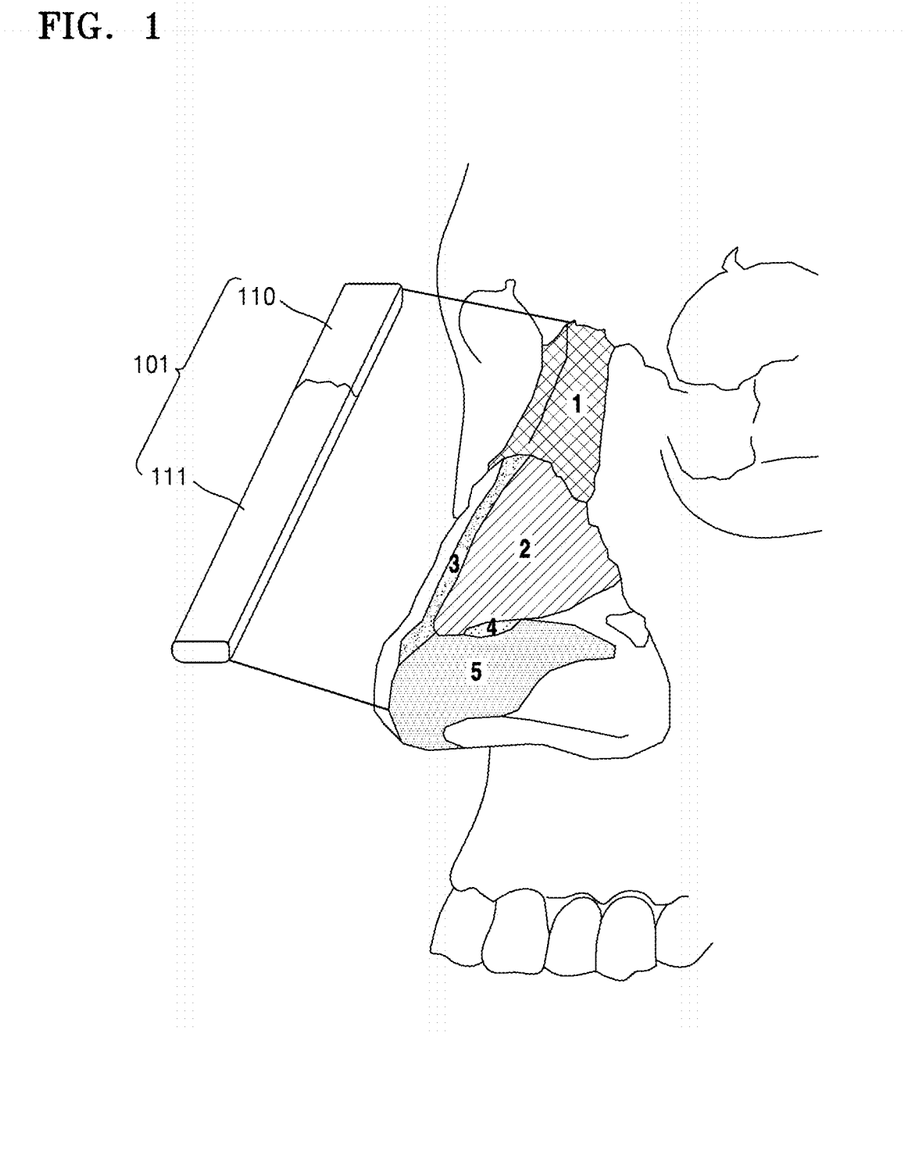
FIG. 1 is a diagram showing a shape of a graft according to an exemplary embodiment or a shape of a second graft according to another exemplary embodiment, in connection with the nasal anatomy.

FIG. 1 is a diagram showing a shape of a graft 101 according to an exemplary embodiment or a shape of a second graft 101 according to another exemplary embodiment. Referring to FIG. 1, the graft 101 or the second graft 101 is for augmentation rhinoplasty, the graft 101 or the second graft 101 including a first compartment 119 consisting of osseous tissue and a second compartment 111 consisting of isolated cartilage tissue and connected with the first compartment through an osteocartilaginous junction 112 (shown in FIG. 2). The graft 101 or the second graft 101 may be isolated from a subject, or may be manufactured as artificial bone, artificial cartilage, or a conjugated product of the artificial bone and the artificial cartilage according to methods obviously known to one of ordinary skill in the art. The graft 101 or the second graft 101 may have a longitudinal length in a range of about 3 cm to about 9 cm, about 4 cm to about 8 cm, or about 5 cm to about 7 cm, a vertical length in a range of about 2 mm to about 15 mm, about 2 mm to about 10 mm, about 3 mm to about 9 mm, or about 3 mm to about 5 mm, and a height in a range of about 0.5 mm to about 3 mm, about 0.5 mm to about 1.5 mm, or about 0.5 mm to about 1.0 mm. The osseous tissue included in the graft 101 or the second graft 101 may include, for example, a part of the nasal bone, and the cartilage tissue included in the graft 101 or the second graft 101 may include, for example, a part of the nasal septum cartilage, a part of the upper lateral nasal cartilage, and/or a part of the alar cartilage. In addition, about ½ to about ⅕ or about ½ to about ¼ of the graft 101 or the second graft 101 may be occupied by the first compartment 101 consisting of the osseous tissue. For example, about 20% to about 50% of the total longitudinal length of the graft 101 or the second graft 101 may be occupied by the first compartment 101 while the rest of the total longitudinal length of the graft 101 or the second graft 101 may be occupied by the second compartment 111.

Figure 2:
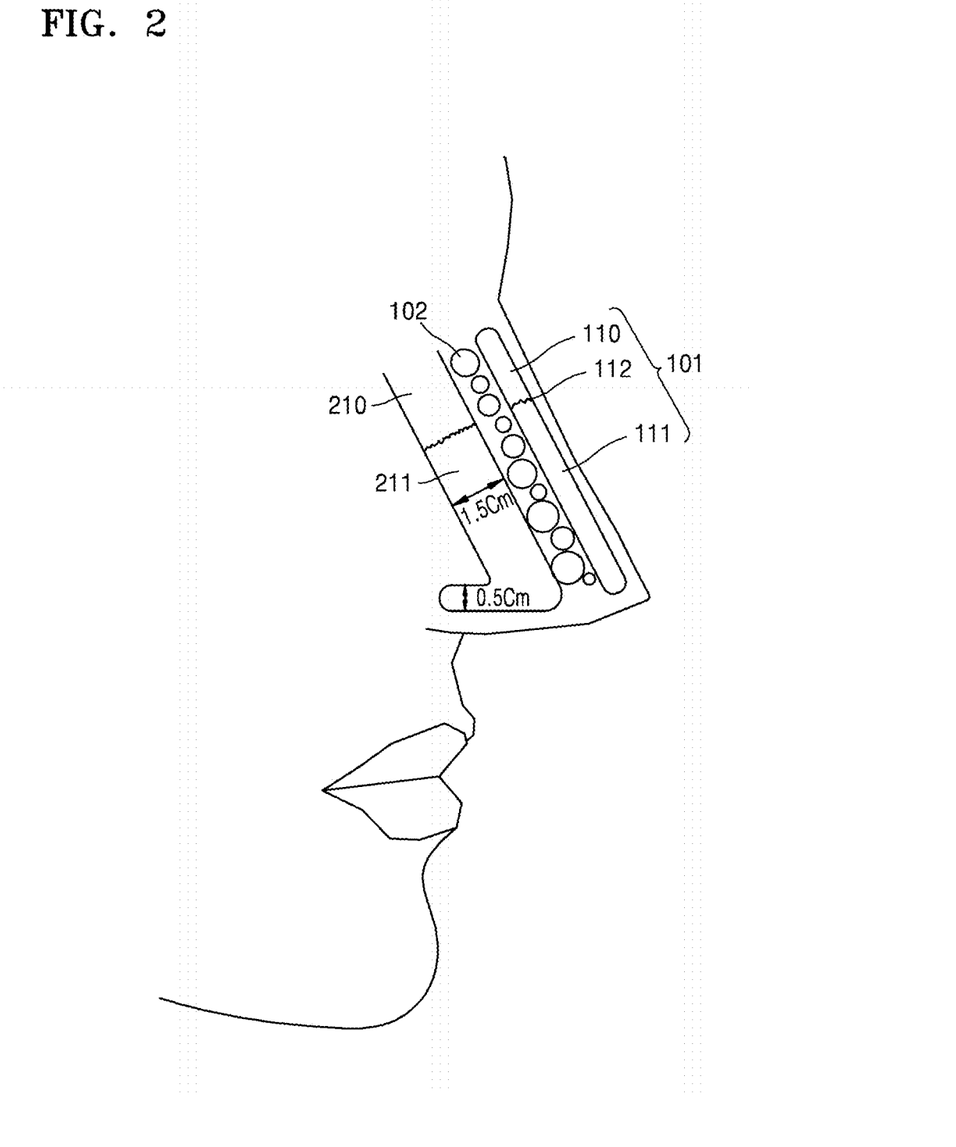
FIG. 2 is a diagram showing a side view of a patient whose nose is inserted with a graft according to an exemplary embodiment or a second graft according to another exemplary embodiment.

FIG. 2 is a diagram showing a side view of a patient whose nose is inserted with the graft 101 according to an exemplary embodiment or the second graft 101 according to another exemplary embodiment.

Referring to FIG. 2, the isolating of the at least one part of the graft 101 or the second graft 101 may be may be performed in a way that a nasal septum (e.g., nasal septum cartilage) remains at least about 0.5 cm in a caudal direction, and remains in a range of about 0.5 cm to about 2.5 cm, about 1.0 cm to about 2.0 cm, or about 1.2 cm to about 1.8 cm in a dorsal direction. The graft 101 or the second graft 101 may inserted into the nasal dorsum below the nasal skin of the patient, thereby forming a new line of nasal dorsum. In addition, a plurality of bone pieces and/or cartilage pieces 102 of the graft 101 according to an exemplary embodiment, or plurality of bone pieces and/or cartilage pieces 102 of the second graft 101 according to another exemplary embodiment may be inserted into a space below the graft 101 or the second graft 101 in a ventral direction to raise a height of the nasal dorsum (i.e., a new line of nasal dorsum) in a dorsal direction. A method of inserting the graft 101 or the second graft 101 is defined the same to the description provided above.

EXAMPLES

In the present inventive concept, a graft was isolated and manufactured according to the exemplary embodiments above in association with 25 call patients, and then, the graft was used for augmentation rhinoplasty. All patients were instructed to fast until 4 hours before surgery, and their age was between 19 and 60 years old.

A part of the patients wanted to have augmentation rhinoplasty for cosmetic purposes, and another part of the patient had congenital or acquired deficiency or deformation of the nose. The patients never had nasal septum surgery before, and wanted to have both augmentation rhinoplasty and nasal tip-plasty. In particular, they were against using an artificial material for augmentation rhinoplasty, and did not allow to use a donor site of other parts of the body (e.g., auricular cartilage or costal cartilage) other than the nose, which is a plastic surgery area.

Example 1

Separation and Manufacture of a Graft

Separation and manufacture of a graft from a patient were performed as follows.

(1) The patient's entire face and inner nose were sterilized with povidone and cleaned with salt brine, and then, the face, except a surgical site of the nose, was covered with a surgical drape.

(2) To anesthetize the patient, both general anesthesia and local anesthesia were performed. 2 ml (1 ampul) of diclofenac sodium (manufactured by Samjin Pharm. Co., Ltd) was injected into a hip of the patient via intramuscular injection, and then, 1 ml (1 ampul) of midazolam (1 mg/ml, manufactured by Myungmoon Pharm. Co., Ltd) and 2 ml (1 ampul) of nalbuphine hydrochloride (10 mg/ml, manufactured by Myungmoon Pharm. Co., Ltd) were injected to the patient via intravenous injection, thereby inducing anesthesia of the patient. Depending on a patient's status, 1 ampul of each of midazolam and nalbuphine hydrochloride was additionally injected to the patient if sedation anesthesia was not induced well. During surgery, 1 to 10 ampuls were used in total. As a local anesthetic drug, 1% lidocaine was used, and 2 mg/kg of lidocaine was injected to a space between the alar cartilage and the upper lateral nasal cartilage, spaced from top to bottom (down to the nasal tip) along the nasal dorsum, an orbital nerve site, a lateral osteotomic site, and a marginal incision.

(3) After conforming that the anesthesia was completely induced, the separation of the graft was performed. Here, the method of approaching the graft used herein was the endonasal approach method. By using scissors designed for cutting the nasal septum and an osteotome were used to separate a graft from the nose in a way that a space having a length about 0.5 cm in a caudal direction and a space having a length of about 1.5 cm in a dorsal direction, were left with from the nasal septum. The graft isolated from the nose consists of nasal bone, nasal septum bone, upper lateral nasal cartilages, and alar cartilages. Here, bone and cartilage formed a composite to be isolated as the graft. The separation of the graft was performed multiple times, thereby isolating 3 to 5 pieces of the graft.

Figure 3:
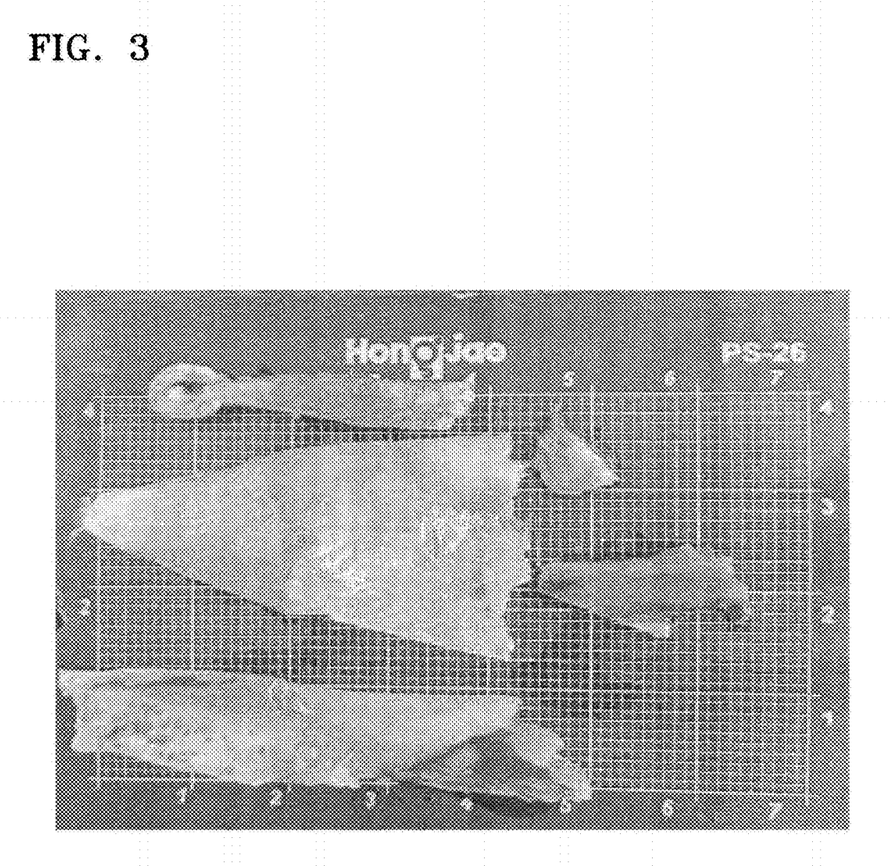
FIG. 3 is an image of a nasal septum (i.e., a first graft) isolated from a patient according to an exemplary embodiment.
Figure 4:
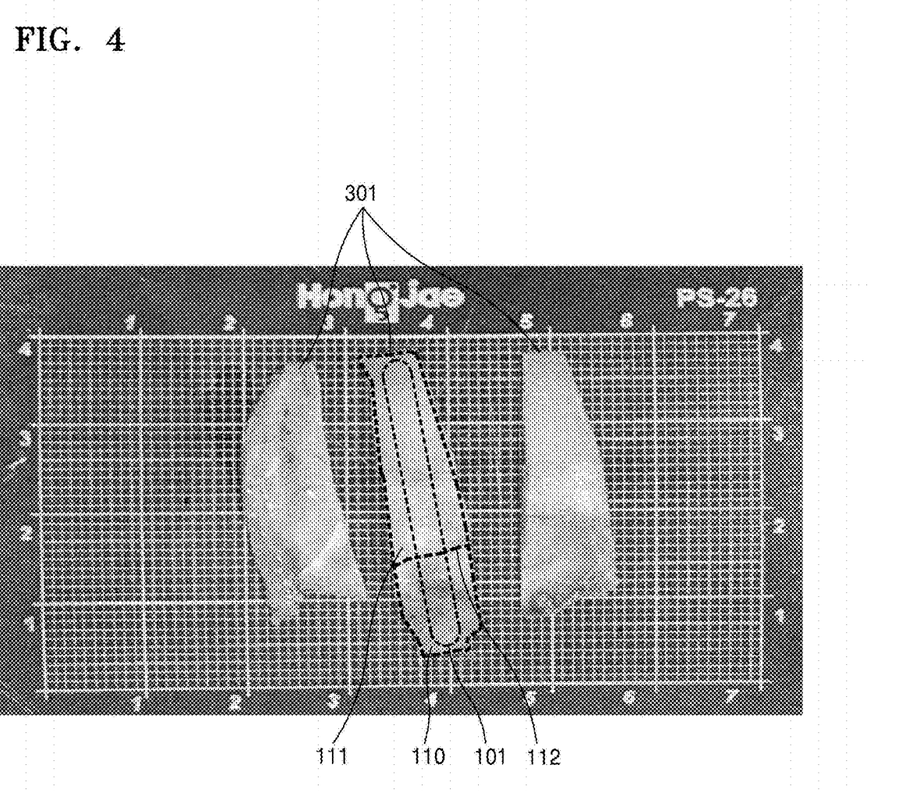
FIG. 4 is an image of a nasal septum (i.e., a first graft) isolated from a patient according to an exemplary embodiment.
Figure 5:
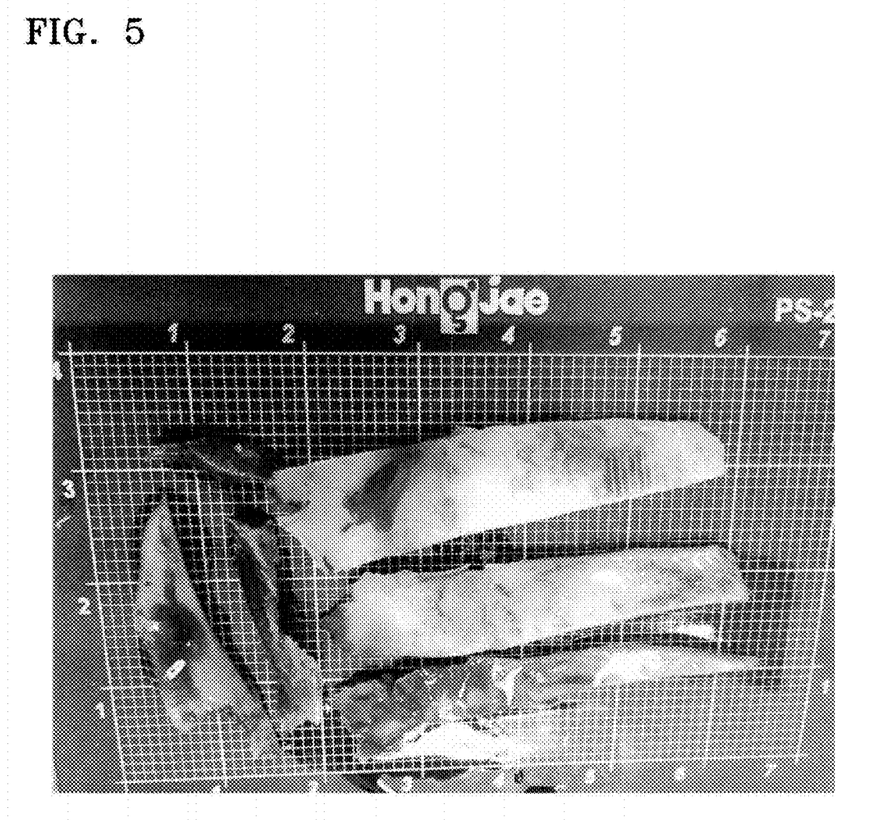
FIG. 5 is an image of a nasal septum (i.e., a first graft) isolated from a patient according to an exemplary embodiment.

FIGS. 3 to 5 are each an image of the nasal septum (i.e., the first graft) isolated from the patients. As shown in FIGS. 3 to 5, at least one composite consist of both nasal bone and cartilages.

Referring to FIG. 4, a plurality of first grafts 301 were isolated from the patient. Here, at least one of the plurality of first grafts 301 was configured to include both the first compartment 110 consisting of the osseous tissue and the second compartment 111 consisting of the cartilage tissue. For example, a part of the one of the first grafts 301 may be incised to manufacture the second graft 101. Here, the second graft 101 was configured to include both the first compartment 110 consisting of the osseous tissue and the second compartment 111 consisting of the cartilage tissue and connecting with the first compartment 101 through the osteocartilaginous junction 112. The second graft may be defined the same with the descriptions provided above.

(4) The largest graft having both bone and cartilage was selected from the grafts isolated from the nose, and then was manufactured as a new graft to be re-inserted into the patient. The new graft was then cut into an appropriate size and shape by using scissors or an osteotome. The size and shape of the new graft were like those shown in FIGS. 6 to 8, or those described above.

Figure 6:
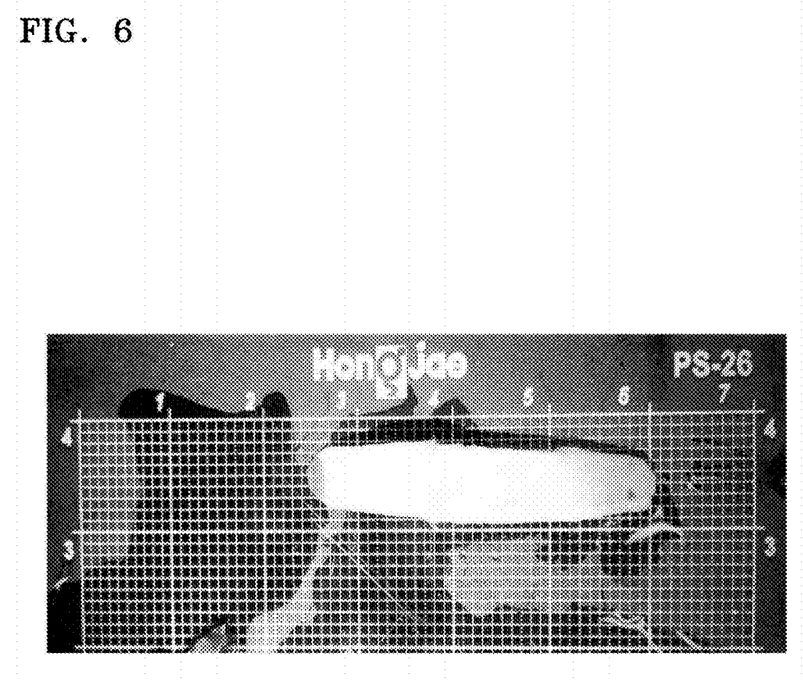
FIG. 6 is an image of a nasal osteocartilaginous graft (i.e., a second graft) prepared by using a nasal septum (i.e., a first graft) isolated from a patient according to an exemplary embodiment.

FIG. 6 is an image of a nasal osteocartilaginous graft (i.e., a second graft) prepared by using the nasal septum (i.e., a first graft) isolated from the patient. The nasal osteocartilaginous graft (i.e., a second graft) may be defined the same with the descriptions provided above.

Figure 7:
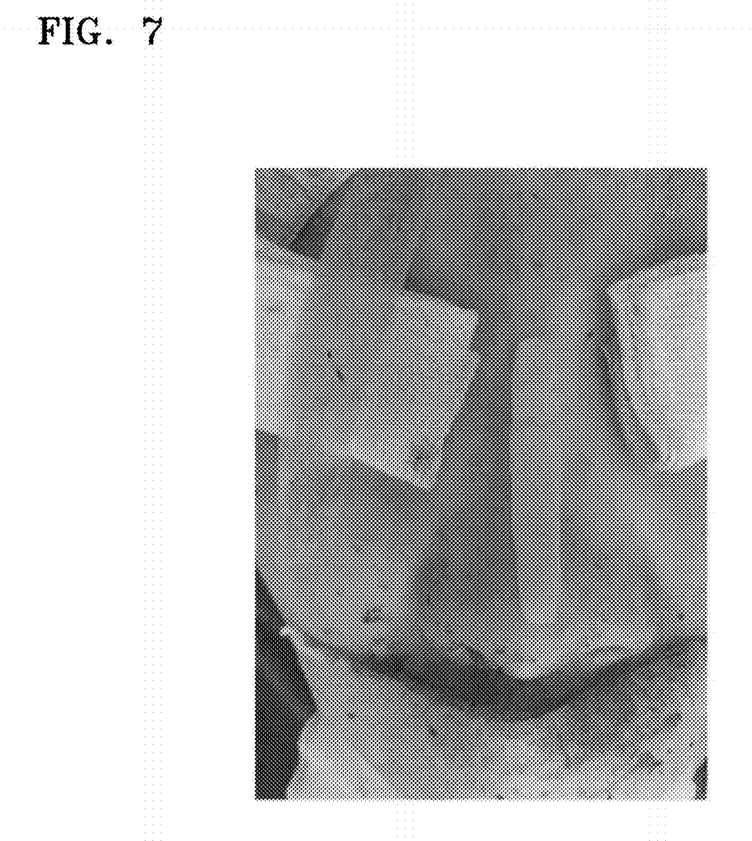
FIG. 7 is an image of a nasal osteocartilaginous graft (i.e., a second graft) placed on a patient's nose bridge, the nasal osteocartilaginous graft being prepared by using a nasal septum (i.e., a first graft) isolated from a patient according to an exemplary embodiment.
Figure 8:
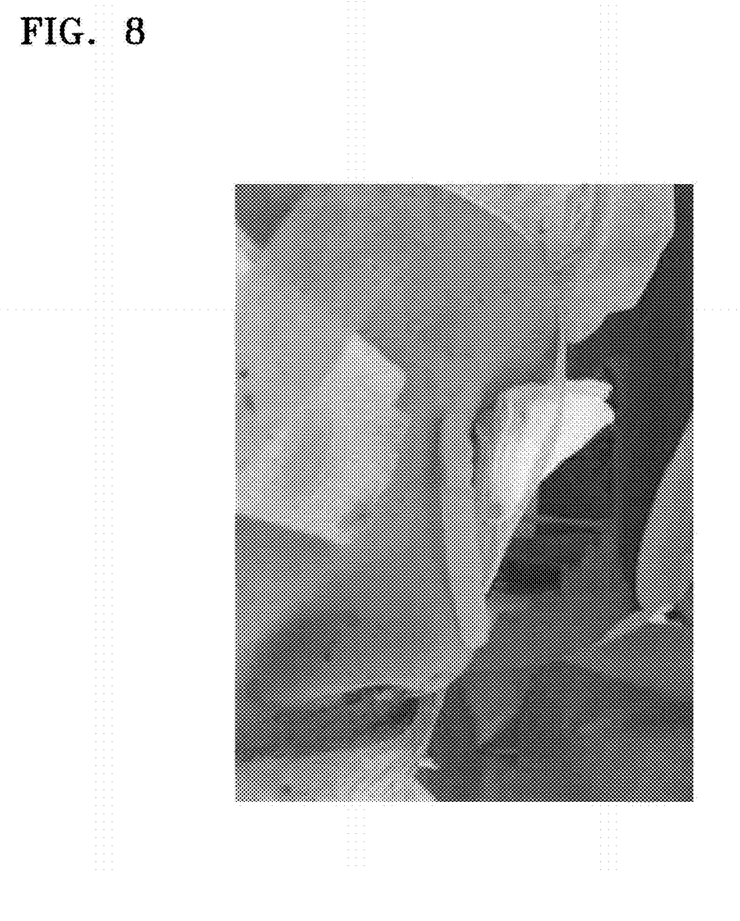
FIG. 8 is an image of a nasal osteocartilaginous graft (i.e., a second graft) placed on a patient's nose bridge, the nasal osteocartilaginous graft being prepared by using a nasal septum (i.e., a first graft) isolated from a patient according to an exemplary embodiment.

FIGS. 7 and 8 are each images of a nasal osteocartilaginous graft (i.e., a second graft) that is placed on a patient's nose bridge (i.e., the nasal dorsum), the nasal osteocartilaginous graft being prepared by using the nasal septum (i.e., a first graft) isolated from the patient.

(5) Afterwards, bone and cartilage left after the graft was manufactured were fractured into pieces. Such bone pieces or cartilage pieces obtained therefrom were used to support the grafts or raise a height of the nose as shown in FIG. 2.

Example 2

Evaluation of the Patient After the Insertion of the Graft and the Performance of the Surgery The insertion of the graft and the graft pieces was performed as follows. First, as shown in FIG. 2, the graft was inserted into a space below the nasal skin. Here, the graft was inserted in a way that a bone part of the graft was placed upward while a cartilage part of the graft was placed downward. Then, the graft pieces were inserted into a space below the inserted graft, thereby forming a new line of nasal dorsum. By referring to the ideal nose index described above, the graft was inserted into the nose, and then, adjusted its position. In addition, nasal-tip plasty was performed in an additional manner. Nasal-tip plasty was performed by using cartilage tissue left after being used for augmentation rhinoplasty. After the insertion of the graft was done in a desired size and shape, a suture was used to suture incision lines, thereby completing the insertion of the graft.

Afterwards, for up to 1 year, the patient's process after the surgery was observed. Consequently, when the method according to an exemplary embodiment was used, autologous tissues were prepared in a sufficient amount so that augmentation rhinoplasty was performed with a desired height. In addition, it was confirmed that the graft was better survived with the originally existing tissues than artificial materials (e.g., silicon materials). In addition, rhinoplasty was easily performed for making a good and natural shape of the nose. As the osseous tissue were grafted on the bones and the cartilage tissue were grafted on the cartilages, the construction of the original anatomical structure of subject was allowed, and it was confirmed that there was no side effects such as a foreign body reaction or the like. In addition, unlike the case of using foreign materials such as silicon materials, there was no translocation of the graft. Regardless of height of the nose, rhinoplasty was completed for a natural and well-made nose in terms cosmetic purposes, as of the original nose.

According to the one or more exemplary embodiments above, a graft and a method of performing augmentation rhinoplasty by using the graft may result in obtaining autologous tissues in a sufficient amount for augmentation rhinoplasty, which enable to raise a height of the nose to a desired level. In addition, a naturally shaped nose may be resulted in an easy manner. As osseous tissues are grafted on bones and cartilage tissues are grafted on cartilages, the construction of the original anatomical structure of a subject can be allowed, and there is an effect that there is no side effect such as a foreign body reaction.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A method of performing augmentation rhinoplasty, the method comprising:
providing at least one first graft by isolating at least one part of a nasal septum from a nose of a subject, wherein the at least one first graft comprises both a first compartment consisting of osseous tissue and a second compartment consisting of cartilage tissue;

manufacturing a second graft for forming a line of nasal dorsum of the subject by excising a part of the at least one first graft, wherein the second graft comprises both a first compartment consisting of osseous tissue and a second compartment consisting of cartilage tissue;

preparing at least two pieces of the first graft by cutting another part of the at least one first graft, which remains after the manufacturing of the second graft, into at least two pieces, wherein the pieces of the first graft include pieces of bone, cartilage, or cartilage tissue;

forming two lines of nasal dorsum by inserting the second graft into a nasal dorsum of the subject; and raising the nasal dorsum in a dorsal direction by inserting one or more of the at least two pieces of the first graft into a space between the two lines of nasal dorsum and positioned in a ventral direction with respect to the second graft that is inserted into the nasal dorsum of the subject.

2. The method of performing augmentation rhinoplasty of claim 1, wherein, in regard to the isolating of the at least one part of the nasal septum, a part of nasal septum cartilage, a part of upper lateral nasal cartilage, and a part of nasal bone form one complex to be isolated from the subject, or the isolating of the at least one part of the nasal septum is carried out by leaving at least about 0.5 cm or less from the nasal septum cartilage in a caudal direction and leaving about 0.5 cm to about 2.5 cm from the nasal septum cartilage in a dorsal direction.

3. The method of performing augmentation rhinoplasty of claim 1, wherein the isolating of the at least one part of the nasal septum is carried out by leaving at least one part of a graft donor site of the subject from mucoperiosteum and mucoperichondrium.

4. The method of performing augmentation rhinoplasty of claim 1, wherein the second graft is prepared to form a line of nasal dorsum having a width in a range of about 5 mm to about 15 mm between two lines of nasal dorsum in view of external appearance, after the second graft is inserted into the nasal dorsum of the subject.

5. The method of performing augmentation rhinoplasty of claim 1, wherein the isolating of the nasal septum, the inserting of the second graft into the nasal septum, or the inserting of the piece of the first graft into the inserted second graft is performed according to an endonasal approach method or an external nasal approach method.

6. The method of performing augmentation rhinoplasty of claim 5, wherein the endonasal approach method comprises a delivery approach method or a nondelivery approach method.

7. The method of performing augmentation rhinoplasty of claim 1, wherein the inserting of the second graft into the nasal septum is carried out in a way that the first compartment of the second graft is arranged in a cranial direction and the second compartment of the second graft is arranged in a caudal direction.

8. The method of performing augmentation rhinoplasty of claim 1, wherein the inserting of the second graft into the nasal septum is carried out in a way that the second graft is inserted from a nasion until a site where an upper lateral nasal cartilage is present is reached.

9. The method of performing augmentation rhinoplasty of claim 1, wherein a second graft and the one or more pieces of the first graft are inserted for rhinoplasty in a way that a height of the nose is uplifted by at least about 4 mm, wherein the height is measured from an imaginary line connecting the nasal bone and the upper lateral nasal cartilage to the nasal skin.

10. The method of performing augmentation rhinoplasty of claim 1, wherein the inserting of the second graft and the inserting of the one or more pieces of the first graft is performed in a way that a ratio of a length of an imaginary line connecting a nasion and a nasal tip to a height of the nasal tip is in a range of about 1:0.5 to about 1:0.8.

11. The method of performing augmentation rhinoplasty of claim 1, wherein the second graft has a longitudinal length in a range of about 3 cm to about 9 cm, a vertical length in a range of about 2 mm to about 15 mm, and a height in a range of about 0.5 mm to about 3 mm.

12. The method of performing augmentation rhinoplasty of claim 1, wherein the osseous tissue comprised in the second graft comprises a part of a nasal bone, and the cartilage tissue comprised in the second graft comprises a part of the nasal septum cartilage and a part of the upper lateral nasal cartilage.

13. The method of performing augmentation rhinoplasty of claim 1, wherein about $\frac{1}{2}$ to about $\frac{1}{5}$ of a longitudinal length of the second graft is occupied by the first compartment consisting of the osseous tissue.

14. The method of performing augmentation rhinoplasty of claim 1, wherein the cartilage tissue comprised in the second graft comprises hyaline cartilage tissue.

15. The method of performing augmentation rhinoplasty of claim 1, wherein the first and second compartments of the second graft are connected to each other through an osteo-cartilaginous junction.

16. The method of performing augmentation rhinoplasty of claim 1, wherein the cartilage tissue that remained after the providing of the at least one first graft for augmentation rhinoplasty is additionally used for performing nasal tipplasty on the support of the nasal tip.

17. The method of performing augmentation rhinoplasty of claim 1, wherein the second graft or the pieces of the first graft are prepared by culturing isolated bone cells and isolated chondrocytes, rather than bone cells and chondrocytes isolated from the human body, in vitro or in vivo.

* * * * *